United States Patent
Crawford et al.

(10) Patent No.: US 9,445,853 B2
(45) Date of Patent: Sep. 20, 2016

(54) INTERVERTEBRAL DOSING DEVICE AND METHOD

(71) Applicant: GLOBUS MEDICAL, INC, Audubon, PA (US)

(72) Inventors: Neil R. Crawford, Tempe, AZ (US); Nicholas Theodore, Paradise City, AZ (US); Mitchell A Foster, Scottsdale, AZ (US)

(73) Assignee: GLOBUS MEDICAL, INC, Audubon, PA (US)

( * ) Notice: Subject to any disclaimer, the term of this patent is extended or adjusted under 35 U.S.C. 154(b) by 269 days.

(21) Appl. No.: 14/030,796

(22) Filed: Sep. 18, 2013

(65) Prior Publication Data

US 2015/0080813 A1    Mar. 19, 2015

(51) Int. Cl.
| | |
|---|---|
| *A61B 17/86* | (2006.01) |
| *A61B 17/34* | (2006.01) |
| *A61M 39/02* | (2006.01) |
| *A61B 17/00* | (2006.01) |
| *A61M 39/24* | (2006.01) |

(52) U.S. Cl.
CPC ......... *A61B 17/864* (2013.01); *A61B 17/3403* (2013.01); *A61B 17/3472* (2013.01); *A61M 39/0208* (2013.01); *A61B 2017/00261* (2013.01); *A61M 2039/2486* (2013.01)

(58) Field of Classification Search
CPC .......... A61B 17/864; A61B 17/3472; A61M 2039/2486
See application file for complete search history.

(56) References Cited

U.S. PATENT DOCUMENTS

| | | | |
|---|---|---|---|
| 6,730,095 B2 * | 5/2004 | Olson, Jr. .............. | A61B 17/70 604/218 |
| 6,852,095 B1 * | 2/2005 | Ray .................... | A61B 17/7097 604/93.01 |
| 2004/0148010 A1 * | 7/2004 | Rush .................. | A61B 17/0469 623/1.13 |

* cited by examiner

*Primary Examiner* — Bradley Osinski

(57) ABSTRACT

Some embodiments of the invention include a cannulated bone screw including a screw shaft with screw thread, a proximal end, a distal end, and a channel extending through the screw shaft. Some embodiments include an inlet port coupled to the channel and extending through the distal end, and an outlet port coupled to the channel by a curved or angled channel region. In some embodiments, the outlet port extends through the screw shaft and exits a side that is substantially parallel to the shaft longitudinal axis. In some embodiments, the cannulated bone screw can form part of a therapy delivery device. In some embodiments, the outlet port extends through a portion of the screw shaft and exits at the distal end. In some embodiments, the valve includes a plunger with a plunger rod within the screw shaft, and a valve seat for control of fluid flow out of the screw.

17 Claims, 10 Drawing Sheets

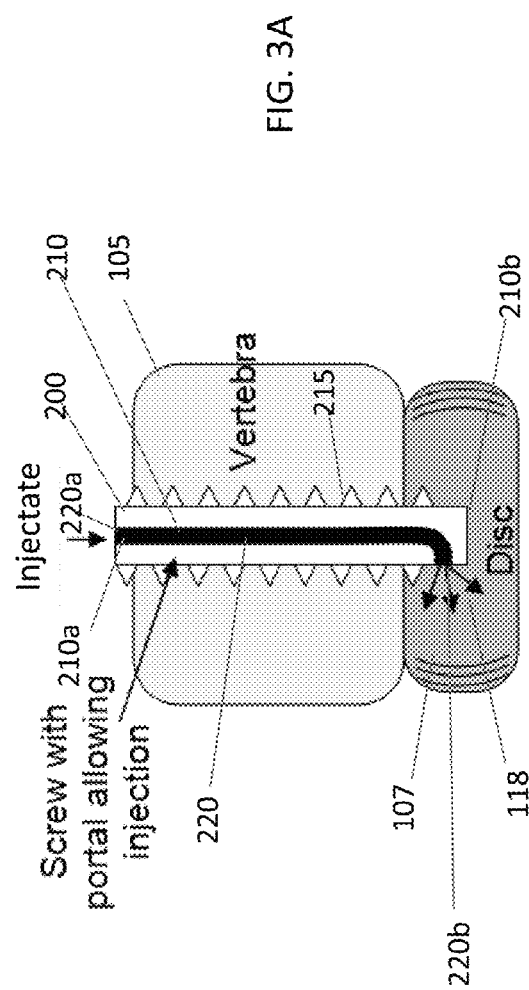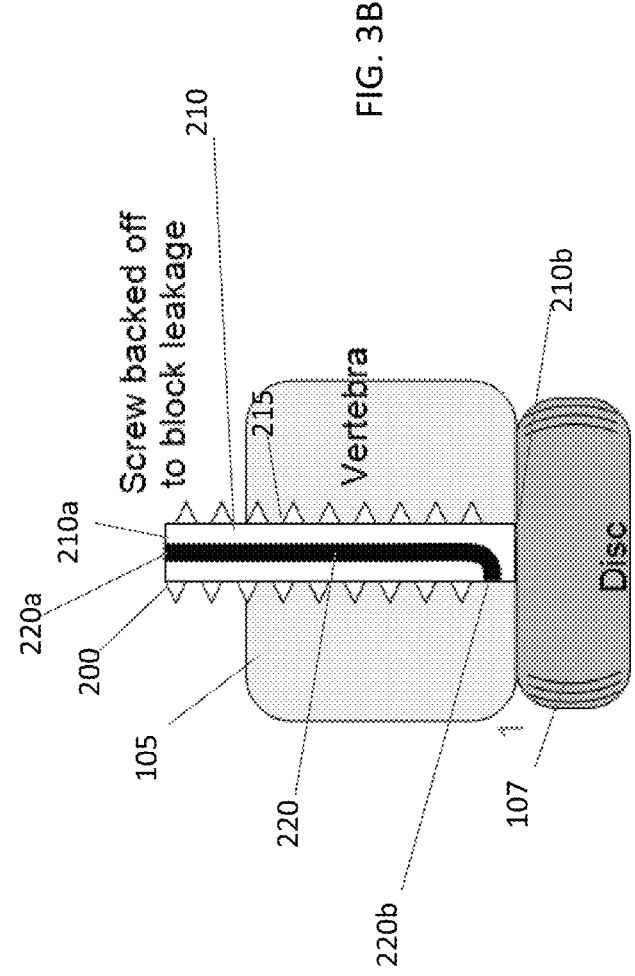

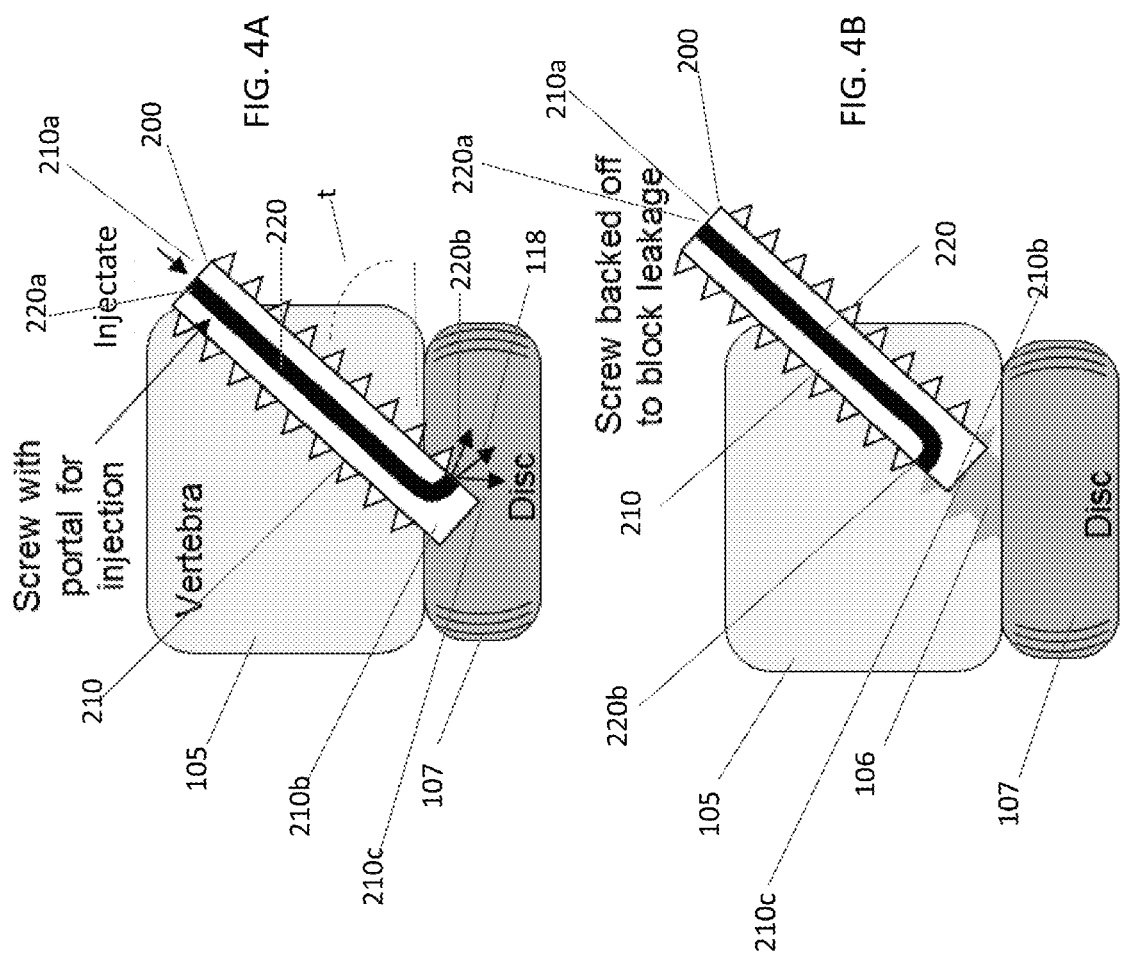

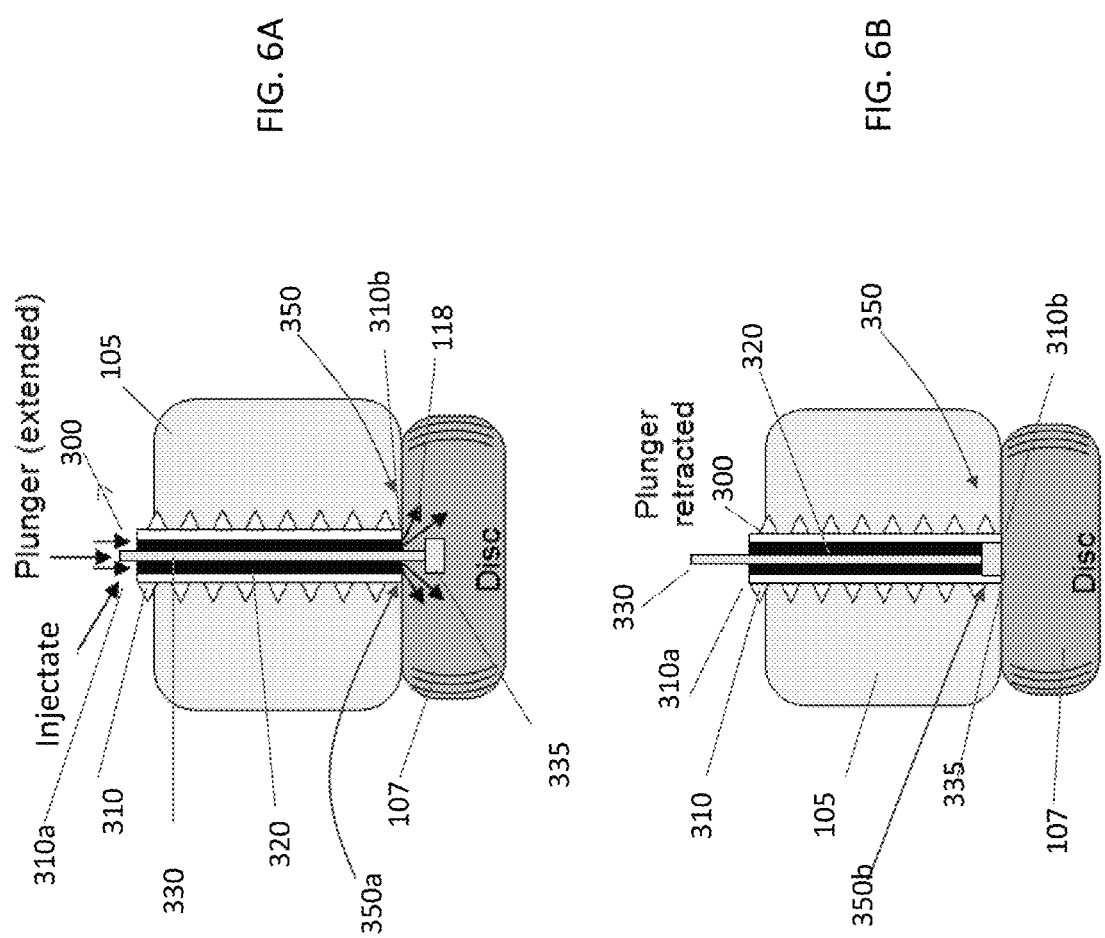

INTERVERTEBRAL DOSING DEVICE AND METHOD

BACKGROUND

Various medical devices and methods are used for percutaneous drug delivery or extraction of biologic material from the intervertebral disc. In general, most current methods for injecting therapeutics into the intervertebral disc have the drawback that some material leaks out of the disc during the procedure. Moreover, the insertion of a drug delivery needle through the annulus can weaken it, thereby making it more susceptible to rupturing. Furthermore, if the patient needs repeated dosing, multiple needle insertions can result in a plurality of punctures, and progressive weakening of the annulus. A single percutaneous insertion capable of repeated dosing without any perforation of the annulus would provide a more flexible and potentially safer method of therapy delivery.

SUMMARY

Some embodiments of the invention include a cannulated bone screw comprising a screw shaft including a screw thread, a proximal end, and a distal end including a tip, and at least one channel extending through the screw shaft. In some embodiments, at least a portion of the at least one channel is substantially parallel to the longitudinal axis of the screw shaft. Some embodiments include a cannulated bone screw with at least one inlet port coupled to the at least one channel and extending through the proximal end, and at least one outlet port coupled to the at least one channel by a curved or angled channel region. In some embodiments, the at least one outlet port extends through the screw shaft and exits at least one side that is substantially parallel to the longitudinal axis of the screw shaft.

In some embodiments, the cannulated screw can comprise a temporary encasement at least partially covering the screw, and in some embodiments, the temporary encasement envelops substantially all the screw thread. In some embodiments, the temporary encasement comprises wax.

Some embodiments comprise a therapy delivery device including a cannulated bone screw comprising a screw shaft including a screw thread, a proximal end, and a screw distal end including a tip, and at least one channel extending through the screw shaft substantially parallel to the longitudinal axis of the screw shaft. In some embodiments of the invention, the therapy delivery device includes at least one inlet port coupled to the at least one channel and extending through the proximal end, and at least one outlet port extending through the screw shaft and exiting at the screw distal end. Some embodiments include at least one valve configured and arranged to control fluid flow into and out of the at least one channel.

In some embodiments, the valve comprises a plunger. In some embodiments, the plunger comprises a plunger rod positioned within the screw shaft and a plunger first end and a plunger second end and a valve seat coupled to the plunger second end. In some embodiments, the valve comprises a closed valve when the plunger is withdrawn so that the valve seat is sealed against the screw distal end, and is configured and arranged to substantially prevent flow into and out of the channel. In some other embodiments, the therapy delivery device comprises an open valve when the plunger is extended so that the valve seat is positioned distal from the screw distal end, and is configured and arranged to enable fluid flow into and out of the channel.

In some embodiments, fluid flow rate through the valve and fluid flow into and out of the cannulated screw is controlled by the plunger position within the screw shaft. Some embodiments include a spring coupled to the plunger. In some embodiments, the spring is configured and arranged to maintain the valve seat sealed against the distal end when the plunger is not forcibly extended. In some further embodiments, the spring is configured and arranged to expand when the plunger is forcibly extended.

Some embodiments include a therapy delivery device comprising at least one subcutaneously implanted dosing reservoir, and at least one tube coupled to a channel and extending through a patient to fluidly couple with the dosing reservoir. In some embodiments, the therapy delivery device is fluidly coupled to a drug delivery needle, and in some embodiments, the reservoir includes at least one drug.

In some embodiments, the valve and other components of the device are bioresorbable. In some embodiments, the plunger comprises bioresorbable material which can include polylactic acid.

DESCRIPTION OF THE DRAWINGS

FIG. 3A illustrates a dose delivery to an intervertebral disc using the cannulated screw of FIG. 2 in accordance with at least one embodiment of the invention.

FIG. 3B illustrates a dose delivery to an intervertebral disc using the cannulated screw of FIG. 2 in accordance with at least one embodiment of the invention.

FIG. 4A illustrates a dose delivery to an intervertebral disc using the cannulated screw of FIG. 2 in accordance with at least one embodiment of the invention.

FIG. 4B illustrates a cannulated screw of FIG. 2 following a dose delivery to an intervertebral disc in accordance with at least one embodiment of the invention.

FIG. 6A illustrates a dose delivery to an intervertebral disc using the cannulated screw depicted in FIG. 5A with plunger extended in accordance with one embodiment of the invention.

FIG. 6B illustrates a dose delivery to an intervertebral disc using the cannulated screw depicted in FIG. 5B with plunger retracted in accordance with one embodiment of the invention.

DETAILED DESCRIPTION

Figure 1:
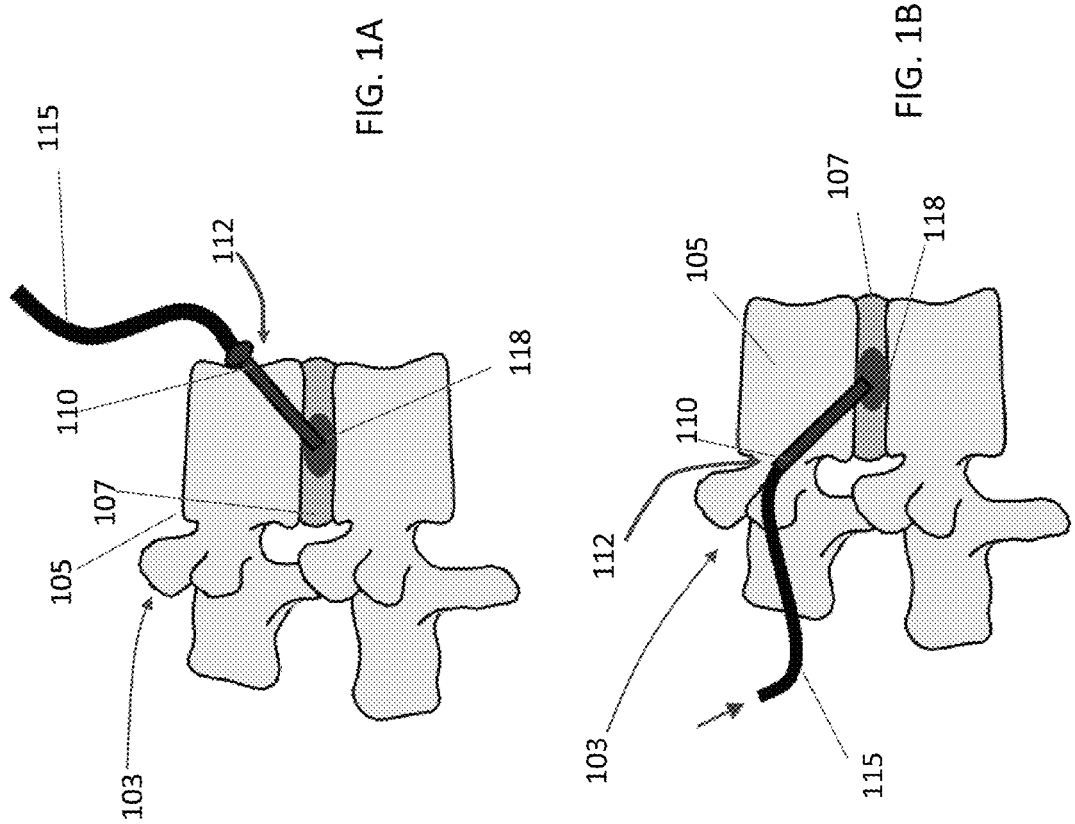
FIG. 1A illustrates a method of delivering therapy to an intervertebral disc using an anterior approach in accordance with at least one embodiment of the invention.
FIG. 1B illustrates a method of delivering therapy to an intervertebral disc using a posterior approach in accordance with at least one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

Some embodiments of the invention provide a system and method for forming a pathway for dosing or injecting a drug to the intervertebral disc by positioning a fluid channel through the vertebral body 105. For example, FIG. 1A illustrates a method of delivering therapy to an intervertebral disc 107 within spinal segment 103 using an anterior approach in accordance with at least one embodiment of the invention. FIG. 1B illustrates a method of delivering therapy to an intervertebral disc 107 of a spinal segment 103 using a posterior approach in accordance with at least one other embodiment of the invention. As shown, therapy delivery can be accomplished using a delivery portal 112 comprising a bone anchor 110 coupled to a tube 115 to enable fluid delivery from the tube 115 through the anchor 110, forming a dosed region 118. Because of the size and shape and variations that may occur in the vertebral body 105, positioning of the delivery portal 112 requires accurate drilling to safely position the bone anchor 115. Furthermore, one of ordinary skill in the art will recognize that the method of delivering therapy to an intervertebral disc 107 using an anterior approach shown in FIG. 1A and posterior approach show in FIG. 1B may include variations to the illustrated trajectories. For example, some embodiments may include forming a delivery portal 112 comprising a bone anchor 110 coupled to a tube 115 to enable fluid delivery from the tube 115 through the anchor 110, forming a dosed region 118 at a trajectory that is selected between the anterior and posterior approach based on a surgeon's preference, the type of therapy, and/or the size and shape and variations that may occur in the vertebral body 105. Moreover, some embodiments may include forming a delivery portal 112 comprising a bone anchor 110 coupled to a tube 115 to enable fluid extraction and/or delivery from and/or to the disc 107 through the tube 115. For example, in some embodiments, the delivery portal 112 may be used in place of or in combination with a bone marrow aspirate kit such as the RETRIEVE® bone marrow aspirate kit. The RETRIEVE® trademark used for bone marrow aspirate kits is a registered trademark of Globus Medical Inc.

In some embodiments, delivery portal 112 can be positioned using a surgical robot. For example, in some embodiments, any one of the cannulated screws 200, 300, 400 described herein and illustrated in FIGS. 2, 3A-3B, 4A-4B, 5A-5B, 6A-6B, 7A-7B, and 8 may be driven by a surgical robot (and optionally viewed with an imaging system) that utilizes a Cartesian positioning system that allows movement of a surgical instrument to be individually controlled in an x-axis, y-axis and z-axis. A surgical robot suitable for this task has been described in U.S. Provisional Patent Application No. 61/662,702 filed on Jun. 21, 2012, U.S. Provisional Patent Application No. 61/800,527 filed on Mar. 15, 2013, and Non-Provisional patent application Ser. No. 13/924,505 filed on Jun. 21, 2013, the entire contents of which are hereby incorporated by reference. As described, the surgical robot can include a base, a robot arm coupled to and configured for articulation relative to the base, as well as an end-effectuator coupled to a distal end of the robot arm. The effectuator element can include the surgical instrument or can be configured for operative coupling to the surgical instrument, and the roll, pitch and yaw rotation of the end-effectuator and/or surgical instrument to be controlled without creating movement along the x-axis, y-axis, or z-axis. The system can be configured to automatically position and rigidly hold the end-effectuator and/or the surgical instrument in accurate alignment with a required trajectory, such as, for example, a selected trajectory of a cannulated screw 200, 300 during insertion procedures. In case of movement of the patient, the system can be configured to automatically adjust the position of the robot to maintain desired alignment relative to an anatomical region of interest.

In some further embodiments, delivery portal 112 can include or comprise a curved, steerable needle (e.g., a nitinol-based needle). In this instance, in some embodiments, steering and penetration could be aided both inside and outside of the body 105 using radiofrequency emitters at the tip of the needle and can comprise elements of the devices and systems described in U.S. Pat. Nos. 8,010,181, 8,219,177, and 8,219,178, the disclosures of which are incorporated herein by reference in their entireties.

Figure 2:
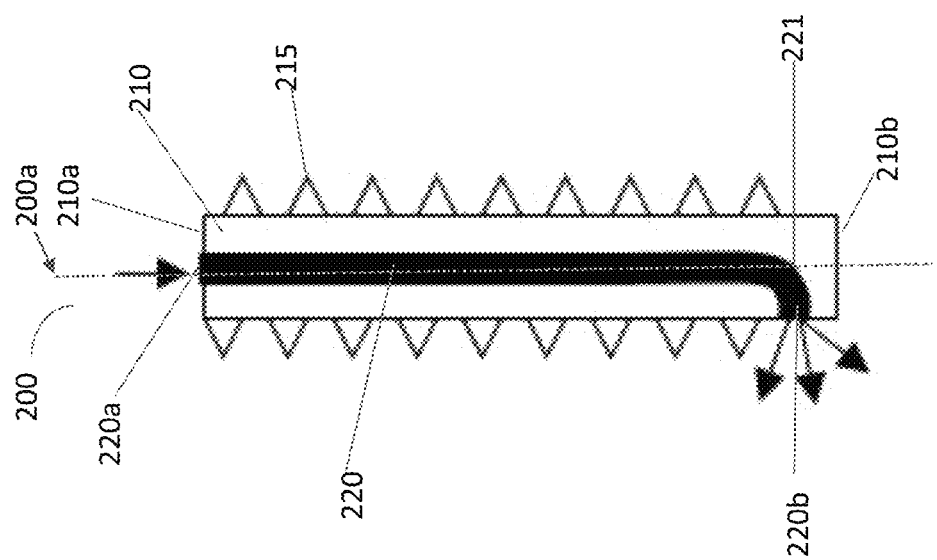
FIG. 2 illustrates a cannulated screw in accordance with at least one embodiment of the invention.

Some embodiments of the invention can include a delivery portal 112 that comprises a cannulated device. For example, FIG. 2 illustrates a cannulated screw 200 in accordance with at least one embodiment of the invention. As shown, in some embodiments, the cannulated screw 200 can include a screw shaft 210 comprising a proximal end 210a and a distal end 210b, and a screw thread 215. In some embodiments, the cannulated screw 200 can also include a channel 220 comprising an inlet port 220a and an outlet port 220b, and a curved or angled channel region 221. As shown, the curved or angled channel region 221 can comprise a channel 220 with a bend of about 90°, enabling dosing proximal to the tip 210c of the screw 200. As shown in FIG. 2, the channel 220 can be positioned about a central axis 200a, and may comprise a diameter of about one third of the diameter of the cannulated screw shaft 210. In some other embodiments, the channel 220 may be more than or less than about a third of the diameter of the shaft 210.

In some embodiments as shown, a substantial portion of the channel 220 may run parallel to the longitudinal axis 220a, whereas at least some portion of the channel 220 may run substantially perpendicular to the central axis 200a. In some other embodiments, the curved or angled channel region 221 can comprise a channel 220 with a bend of less than about 90°, whereas in some further embodiments, the curved or angled channel region 221 can comprise a channel 220 with a bend of greater than about 90°. As shown, in some embodiments, the curved or angled channel region 221 can comprise a channel 220 with a bend of about 90°, enabling dosing proximal to the tip 210c of the screw 200

As shown, in some embodiments, the diameter of the inlet port 220a is substantially identical to the diameter of the outlet port 220b. In some other embodiments, the diameter of the inlet port 220a is greater than the diameter of the outlet port 220b (not shown), whereas in some further embodiments, the diameter of the inlet port 220a is less than the diameter of the outlet port 220b. In some other embodiments, the diameter of either of the inlet port 220a or the outlet port 220b can be different from the diameter of the channel 220.

Some embodiments include a cannulated screw 200 with more than one output 220b (not shown). For example, some embodiments can include a plurality of output 220b coupled to a plurality of curved or angled channel region 221, each fluidly coupled to the channel 220. In some embodiments, the plurality of outputs 220b will form an exit on the same side of the cannulated screw 200 (i.e., the side parallel with the longitudinal axis 220a), whereas in other embodiments, the cannulated screw 200 can include outputs 220b on both sides.

Some embodiments include a cannulated screw 200 with more than one inlet port 220a (not shown). For example, some embodiments may include a plurality of inlet port 220a, each capable of coupling to the same or different dose composition, and each capable of delivering a dose at the same or different flow rates.

In some other embodiments, the cannulated screw 200 can include a plurality of channels 220 (not shown). For example, some embodiments can include two or more of the channels 220 shown in FIG. 2, each fluidly isolated from each other and distributed within the shaft 210.

Some embodiments include methods of delivering a therapy to an intervertebral disc 107 using at least one embodiment of the cannulated screw 200 described earlier and illustrated in FIG. 2. For example, FIGS. 3A and 3B illustrates a dose delivery to an intervertebral disc 107 using the cannulated screw 200 of FIG. 2 in accordance with at least one embodiment of the invention. FIGS. 4A and 4B illustrate a dose delivery to an intervertebral disc 107 using the cannulated screw 200 of FIG. 2 in accordance with at least one alternative embodiment of the invention. In some embodiments, a dose delivery can proceed by positioning the cannulated screw approximately perpendicular to the intervertebral disc 107 (as shown in FIGS. 3A-3B), whereas in other embodiments, the cannulated screw 200 can be driven into the intervertebral disc 107 at an angle (shown as angle t in FIGS. 4A-4B).). If angle t is 0°, FIGS. 4A-4B are essentially the same as FIGS. 3A-3B. In some embodiments, angle t is about 45° as shown in FIGS. 4A-4B. In some other embodiments, the angle t may be less than about 45°, whereas in other embodiments, angle t may be greater than about 45°.

An example of an embodiment in which the angle t in FIGS. 4A-4B would be near 0° is a transsacral approach, such as is used in the TranS1 AxiaLIF procedure (Baxano Medical), where the delivery device would be inserted through the sacrum and into the L5-S1 disc. Another embodiment in which the angle t would be near 0° is a procedure in which multiple vertebrae are penetrated to reach the target. For example, if a cannula entered the disc or bone at or near T12-L1 disc space and then advanced caudally through the L1 vertebral body, crossing the L1-L2 disc and then the L2 vertebral body before deploying in the L2-L3 disc space, the entry into the L2-L3 disc space would resemble FIGS. 3A-3B or FIGS. 4A-4B with angle t=0°. An example of an embodiment in which the angle t would be near 45° is a posterolateral approach to the spine with a trajectory aimed 45° caudally toward the posterolateral wall of the L2 vertebra, with penetration into the L2-L3 disc space.

As shown, in some embodiments, once a cannulated screw 200 has been driven through the vertebral body 105 and into the intervertebral disc 107, therapy can be administered through the channel 220 and injected into the disc 107 to form a dosed region 118.

In some embodiments, the therapy can comprise delivery of at least one drug (i.e. at least one chemical compound classified as a pharmaceutical, including, but not limited to an analgesic or a steroid). In some embodiments the therapy can comprise delivery of at least one biologic (i.e., at least one biomolecular drug, including, but not limited to growth factors and genetic materials). In some embodiments, the therapy can comprise delivery of at least one bioactive material, including, but not limited to a bone powder, a bioactive ceramic, or a hydroxyapatite, or proteins (such as bone morphogenetic protein or BMP) and/or mixtures thereof. In some further embodiments, the therapy can comprise delivery of at least one cellular composition (e.g., cell injections for intervertebral disc repair, including, but not limited to, stem cells). In some further embodiments, the therapy can comprise delivery of at least one matrix material (e.g., a therapy containing at least one tissue engineering matrix material, including, but not limited to, living tissue, transplanted tissue, or engineered tissue).

As shown in FIG. 4B, in some embodiments, once therapy delivery has been completed, the screw 200 can be counter-rotated (i.e., rotated in a direction opposite to the direction used to percutaneously insert the screw 200) to draw the screw 200 away from the disc 107 at least partially so as to move the outlet port 220b out of the intervertebral disc region and into the vertebral body. In some embodiments, this withdrawal of screw 200 can prevent further fluid delivery. In some embodiments, the screw 200 can be left in the withdrawn state and later moved back into the intervertebral disc for further therapy delivery. In some other embodiments, the screw 200 can be completely withdrawn from the vertebral body 105 and the patient. In some other embodiments, a conventional plug can be inserted or screwed into the cannulation. For example, the plug can consist of a permanent material such as PEEK, nylon, or metal, and can be inserted in a threaded cannulation or friction fit or otherwise clamped or adhered and held inside a smooth cannulation in the screw. In some other embodiments, the plug and/or screw 200 can consist of a biocompatible and/or bioresorbable material such as polylactic acid ("PLA") that would degrade over time and be replaced by connective tissue or bone. In this instance, a PLA-based screw 200 and plug have the benefit that no permanent foreign body is left in the patient after dosing treatment of the disc 107 is completed.

Figures 5A, 5B:
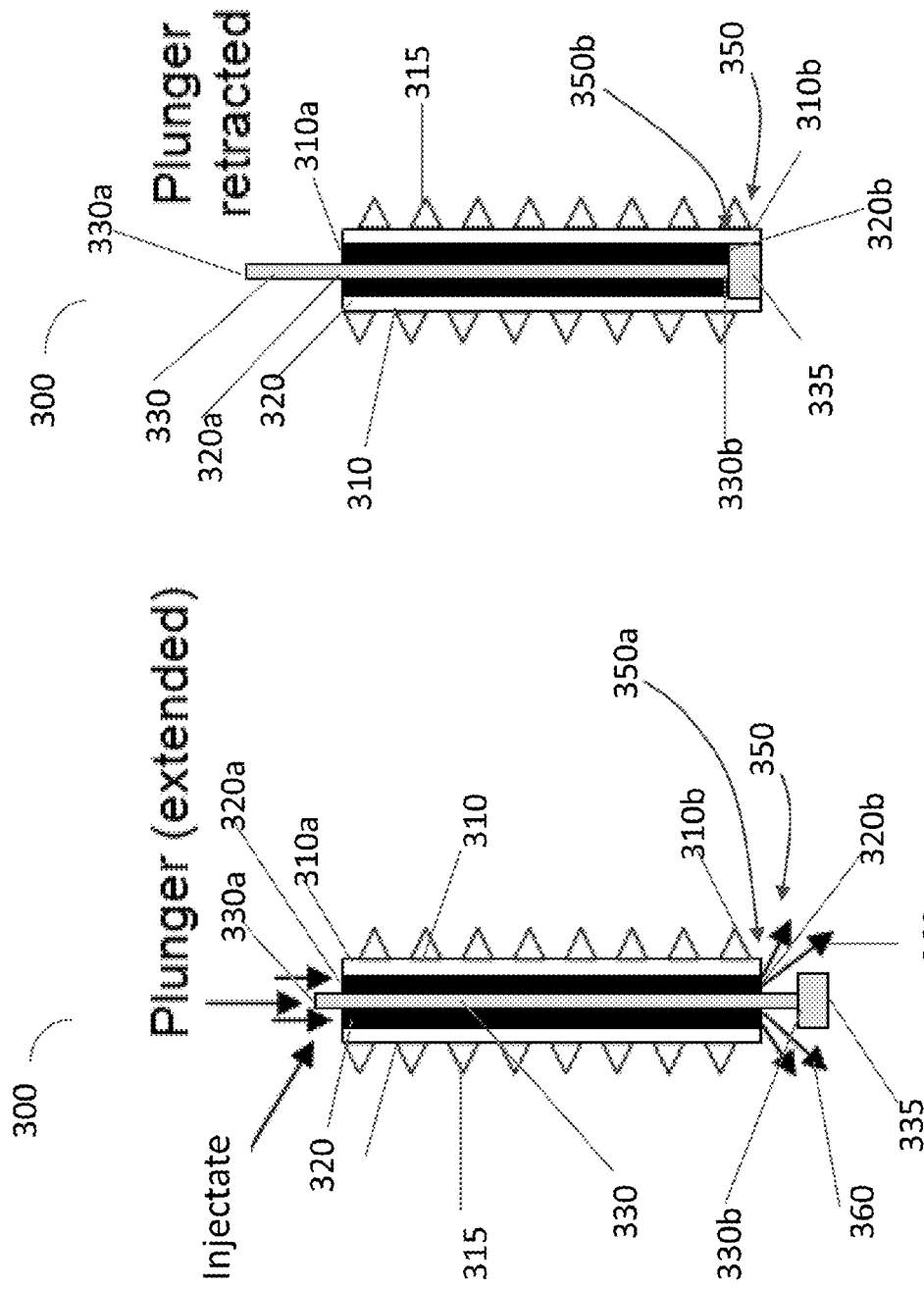
FIG. 5A illustrates a cannulated screw with plunger extended in accordance with another embodiment of the invention.
FIG. 5B illustrates a cannulated screw with plunger retracted in accordance with another embodiment of the invention.

Some embodiments can include alternative screw architectures and alternative methods of controlled delivery and flow of a therapy through a screw. For example, as shown in FIGS. 5A-5B, 6A-6B, and 7A-7B, in some embodiments the channel 320 can extend longitudinally through the screw shaft 310 including an inlet port 320a extending to and exiting the proximal end 310a, and an outlet port 320b extending to and exiting the distal end 310b. In some other embodiments (not shown), the screw assembly 300 can include more than one channel 320, each channel 320 extending longitudinally through the screw shaft 310 and including an inlet port 320a extending to and exiting the proximal end 310a and an outlet port 320b extending to and exiting the distal end 310b. Moreover, some embodiments include a valve 350 comprising a moveable plunger 330. Some embodiments include a plunger 330 including a valve seat 335 capable of forming a valve 350, moveable to an open position (open valve 350a) or a closed position (closed valve 350b). FIG. 5A illustrates a cannulated screw assembly 300 with plunger 330 extended forming an open valve 350a in accordance with one embodiment of the invention, and FIG. 5B illustrates a cannulated screw assembly 300 with plunger 330 retracted forming a closed valve 350b in accordance with another embodiment of the invention. In some embodiments, the cannulated screw assembly 300 can include a screw shaft 310 comprising a proximal end 310a and a distal end 310b, and screw thread 315. As shown, in some embodiments, the valve 350 can be positioned at the distal end 310b. However, in other embodiments, the valve 350 can be positioned anywhere in the line of fluid flow, and may be separate from the screw shaft 310.

In some embodiments, the screw assembly 300 can include a channel 320 comprising an inlet port 320a, and outlet port 320b, and a plunger 330. The plunger 330 can comprise a plunger rod 331, a first end 330a, and a second end 330b and a plunger valve seat 335 coupled to the second end 330b. As depicted by FIGS. 5A and 5B, movement of the plunger 330 with respect to the distal end 310b can create a valve 350 capable of an open valve 350a position and closed valve 350b position. As depicted in FIG. 5A, when the second end 330b is extended, the plunger valve seat 335 can move away from the distal end 310b to create an open valve 350a. In some embodiments as shown, an open valve 350a can enable a dose flow 360. In some embodiments, when the second end 330b is retracted, the plunger valve seat 335 can move toward the distal end 310b to create a closed valve 350a. As depicted in FIG. 5B, in some embodiments, a closed valve 350b can prevent a dose flow 360.

In some embodiments, the valve 350 can be used to control a dosing region 118. For example, FIG. 6A illustrates a dose delivery to an intervertebral disc 107 using the cannulated screw assembly 300 depicted in FIG. 5A with plunger 330 extended in accordance with one embodiment of the invention, and FIG. 6B illustrates a dose flow 360 to an intervertebral disc 107 using the cannulated screw assembly 300 depicted in FIG. 5B with plunger 330 retracted in accordance with one embodiment of the invention. As shown, the open valve 350a can allow the formation of a dosing region 118. In some embodiments, once dosing is complete, or prior to dose flow 360, a closed valve 350b can be formed by retracting the plunger 330 to sealingly couple the plunger valve seat 335 with the distal end 310b.

In some embodiments, the valve 350 can be controlled by movement of the plunger 330 to vary therapy delivery. In some embodiments, by positioning the plunger 330 in various extended positions, a dose flow 360 may be controlled. For example, FIG. 6B shows the valve seat 335 fully retracted into the channel 320, however the valve seat 335 need not be fully retracted into the channel 320 to prevent dose flow 360. Further, in some embodiments (not shown), the rate of formation of the dosing region 118 (i.e., the flow rate of the dose flow 360) may be controlled by positioning the valve seat 335 adjacent to the distal end 310b (but not entering the channel 320). By controlling the spacing between the valve seat 335 and the distal end 310b, the rate of dose flow 360 may be controlled. Additionally, in some embodiments, travel of the plunger 330 from a retracted position toward the distal end 310b can drop pressure of the dose flow 360 from a higher storage pressure to a desired dosing pressure.

Figure 7A:
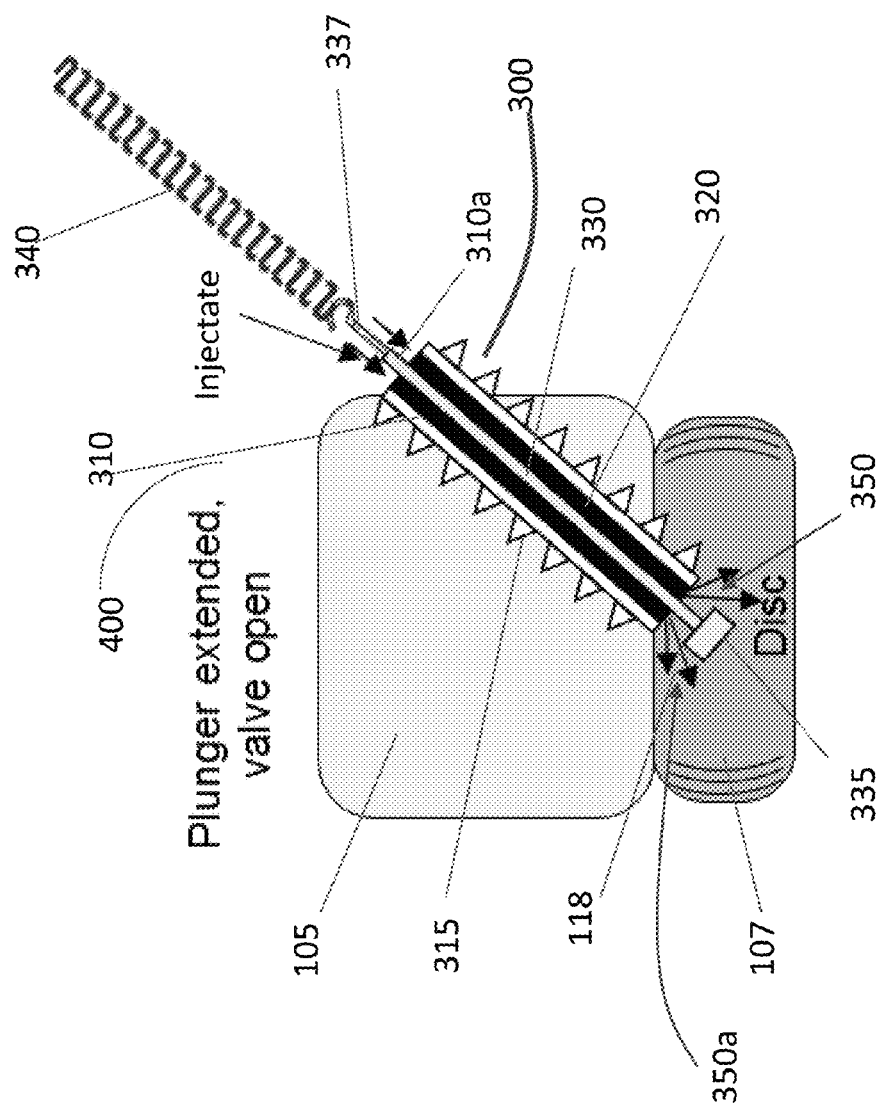
FIG. 7A illustrates a dose delivery to an intervertebral disc using a cannulated screw with plunger extended in accordance with another embodiment of the invention.
Figure 7B:
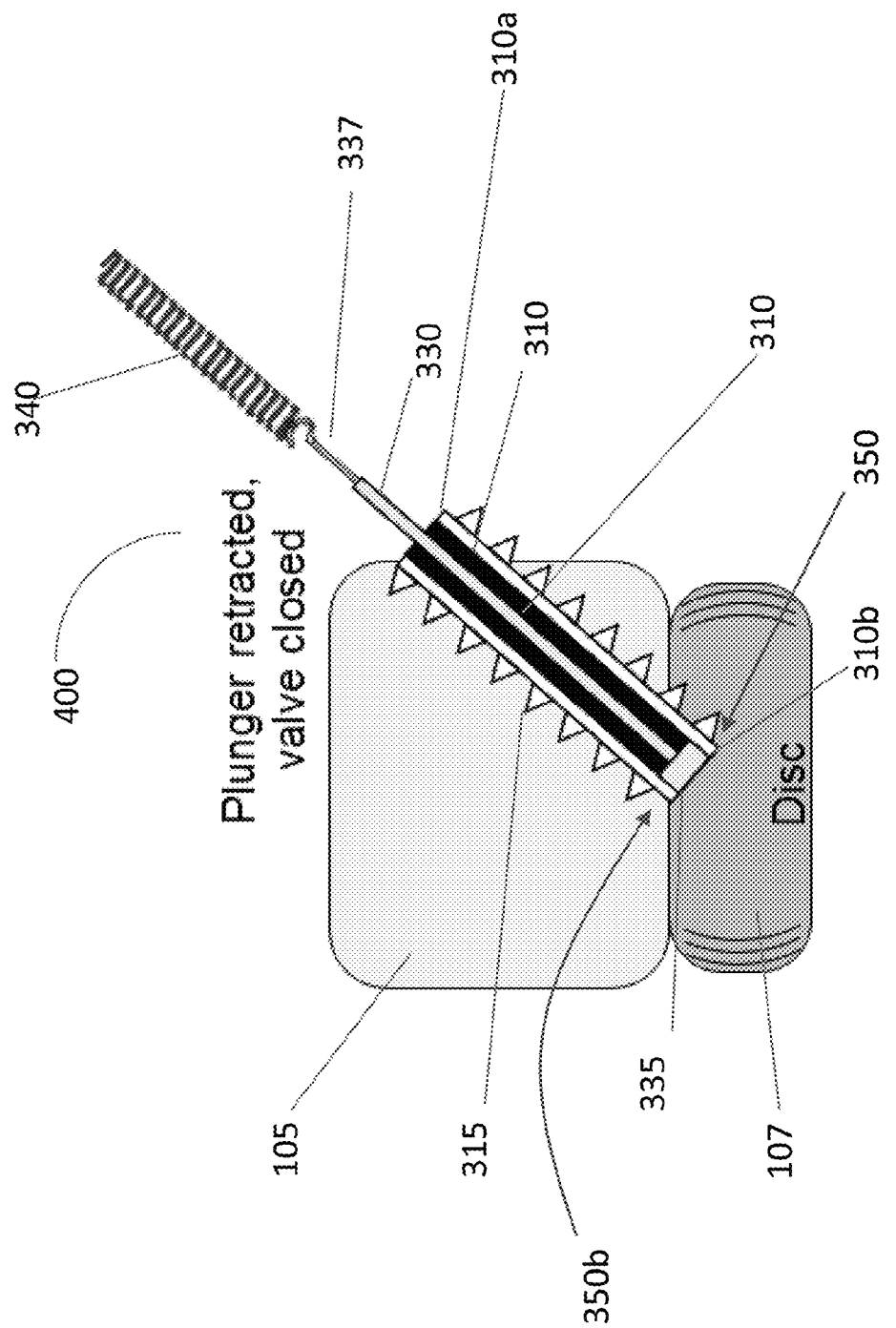
FIG. 7B illustrates a dose delivery to an intervertebral disc using a cannulated screw with plunger retracted in accordance with another embodiment of the invention.

In some embodiments, the plunger 330 can be moved by gripping and moving the first end 330a of the plunger 330. For example, in some further embodiments, the plunger 330 can be retracted using a coupled spring 340 under tension. FIG. 7A illustrates a dose delivery to an intervertebral disc 107 using a cannulated screw assembly 400 with plunger 330 extended in accordance with another embodiment of the invention, and FIG. 7B illustrates a dose delivery to an intervertebral disc 107 using a cannulated screw assembly 400 with plunger 330 retracted in accordance with another embodiment of the invention. As shown, in some embodiments, the plunger can be coupled to a spring 340 by a connecting rod 337. In some embodiments, a plunger 330 can be manually retracted and extended, or can be actuated by a conventional valve mechanism where pressure from the outside (i.e., injection of a fluid into the channel 320) opens the valve 350 but pressure from the inside (i.e., fluid in the disc 107), and possibly additionally force from a spring 340 (or other retractor) closes the valve 350. For example, in some embodiments, the spring 340 is configured and arranged to maintain the valve seat 335 sealed against the distal end 310b when the plunger 330 is not forcibly extended, and in some further embodiments, the spring 340 is configured to expand when the plunger 330 is forcibly extended.

Figures 8A, 8B:
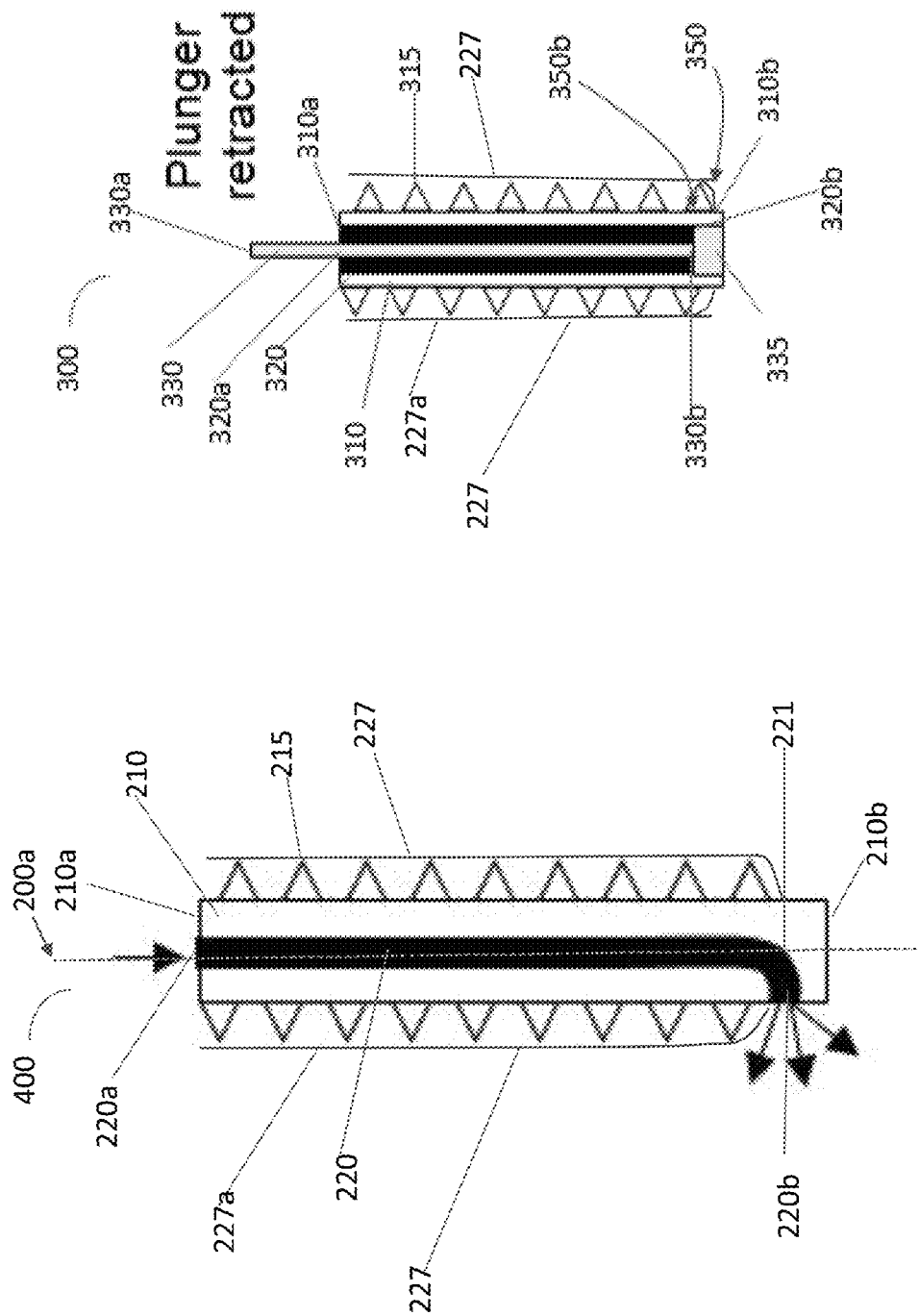
FIG. 8A illustrates a cannulated screw including a temporary encasement in accordance with some embodiments of the invention.
FIG. 8B illustrates a cannulated screw including a temporary encasement in accordance with another embodiment of the invention.

Percutaneous insertion and placement of a bone screw can result in tissue injury. For example, during the insertion procedure, the screw threads may become entangled with connective tissues between the entry point and a bone fixation region which may lead to severe trauma and/or infection. Some embodiments include cannulated bone screws that include a temporary encasement 227, described in detail in the co-pending U.S. patent application Ser. No. 14/021,846 filed on Sep. 9, 2013. For example, FIG. 8A illustrates a cannulated screw 400 including a temporary encasement 227 in accordance with some embodiments of the invention, and FIG. 8B illustrates a cannulated screw 400 including a temporary encasement 227 in accordance with another embodiment of the invention. As depicted, in some embodiments, a temporary encasement 227 can at least partially envelop the screw shaft 210, 310. For example, as shown in FIG. 8A, in some embodiments, a temporary encasement 227 can at least partially envelop the screw 100 covering at least the screw threads 215. In some embodiments, the temporary encasement 227 may comprise a coating that forms a smooth bullet-shaped surface over at least the screw threads 215 and shaft 210. In some embodiments, the temporary encasement 227 can include a substantially smooth outer surface 227a. Further, as shown in FIG. 8B, in some embodiments, a temporary encasement 227 can at least partially envelop the screw assembly 300, covering at least the screw threads 315. In some embodiments, the temporary encasement 227 may comprise a coating that forms a smooth bullet-shaped surface over at least the screw threads 315 and shaft 310. In some embodiments, the temporary encasement 227 may comprise a coating that forms a smooth surface over at least the screw threads 315 and shaft 310 extending from the proximal end 310a to the distal end 310b. In some embodiments, the temporary encasement 227 can include a substantially smooth outer surface 227a.

In some embodiments, the temporary encasement 227 may have sufficient hardness to allow the bone screw 400 to penetrate through soft tissues such as muscle substantially intact, but soft and/or brittle enough to allow the temporary encasement 227 to crumble and/or substantially depart from one or more of the screw shaft 210, the screw thread 215 during penetration into the vertebral body 105. In some other embodiments, the temporary encasement 227 may be at least partially removed from the screw 400 upon entering the body 105 (i.e., at least some fraction of the temporary encasement 227 may remain at an interface between the body 105 and the screw shaft 210).

In some embodiments, the temporary encasement 227 may have sufficient hardness to allow the bone screw 300 to penetrate through soft tissues such as muscle substantially intact, but soft and/or brittle enough to allow the temporary encasement 227 to crumble and/or substantially depart from one or more of the screw shaft 310, the screw thread 315 during penetration into the vertebral body 105. In some other embodiments, the temporary encasement 227 may be at least partially removed from the screw 300 upon entering the body 105 (i.e., at least some fraction of the temporary encasement 227 may remain at an interface between the body 105 and the screw shaft 310).

In some embodiments, the temporary encasement 227 comprises a biocompatible material. In some embodiments, the biocompatible material can be an osteoinductive, a hemostatic, and or a bacteriocide. Some embodiments include a temporary encasement 227 comprising a therapeutic, and in some embodiments, the therapeutic is dispersed within the temporary encasement 227. In some embodiments, the temporary encasement 227 comprises a wax. In some embodiments, when the temporary encasement 227 comprises a material that comprises an osteoinductive, and/or hemostatic, and/or bacteriocidal, after driving the screw into bone, the presence of residual material derived from the encasement 227 in and around the screw-bone interface may provide therapeutic value.

Figure 9:
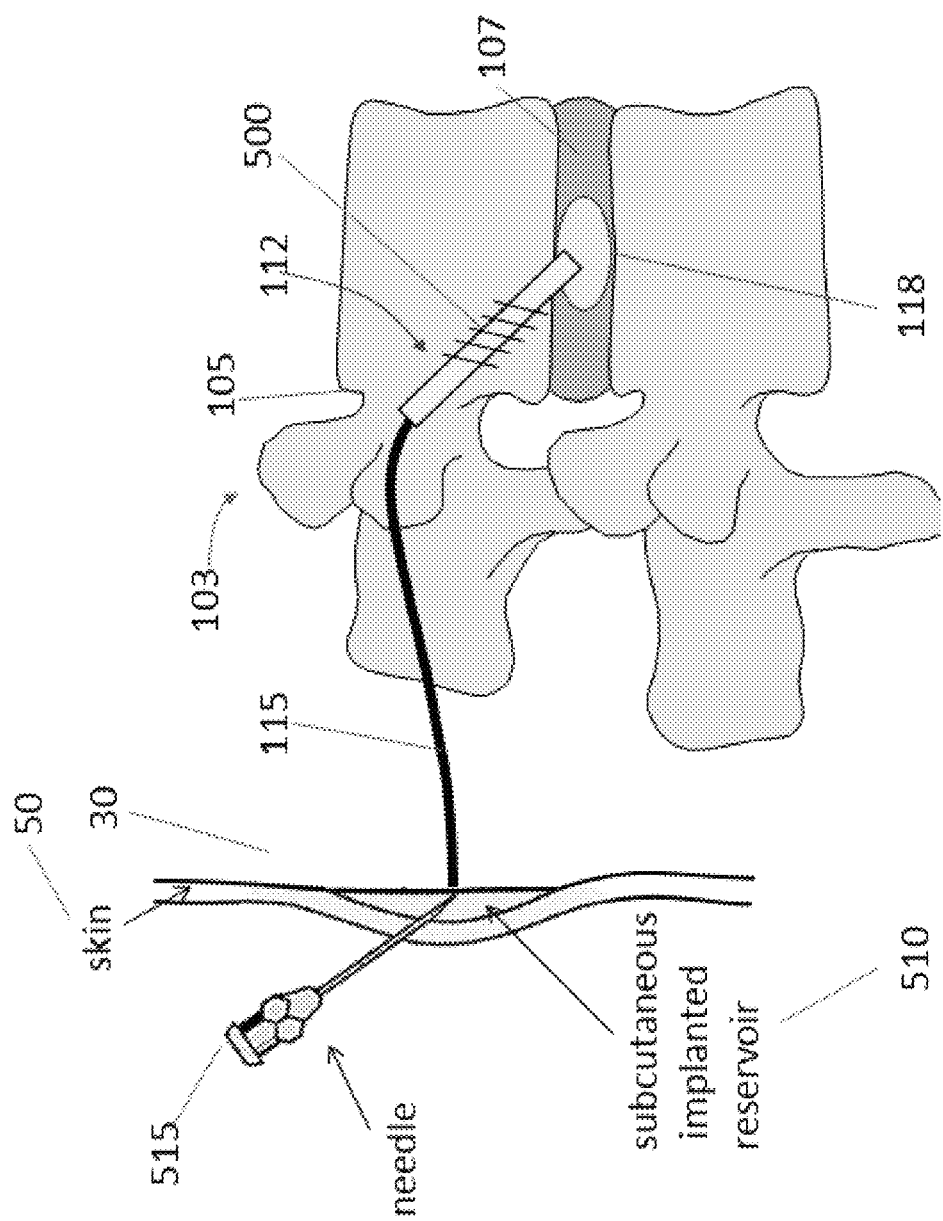
FIG. 9 illustrates a dose delivery to an intervertebral disc using dosing from a patient implanted drug delivery reservoir in accordance with some embodiments of the invention.

A clinically proven method for periodic re-dosing of the brain includes the Ommaya reservoir intraventricular catheter system. The system can be used for drug delivery and aspiration of cerebrospinal fluid. This device is implanted subcutaneously and consists of an elastic reservoir whose membrane can be penetrated by a needle and refilled with a syringe. After withdrawing the needle, the membrane reseals itself and the wound from needle puncture heals. Some embodiments can include a similar method for use with the dosing devices described herein. For example, in some embodiments, the dosing device 500 shown in FIG. 9 can be any one of the cannulated screws or screw assemblies 200, 300, 400 described above and illustrated in FIGS. 2, 3A-3B, 4A-4B, 5A-5B, 6A-6B, 7A-7B, and 8A-8B. In some embodiments, when connected to the dosing device 500, the reservoir 510 can enable periodic treatment of the disc 107 by injection of liquid (e.g., a drug) into the reservoir 510 using a needle 515 piercing the skin 50 of a patient. In some embodiments, for example, therapy delivery can proceed using the dosing device 500 where drug delivery to the patient 30 uses at least one subcutaneously implanted dosing reservoir 510 and at least one tube 115 coupled to a channel within the delivery portal 112 (e.g., a channel 320 of cannulated screw assemblies 300, 400, or a channel 220 of cannulated screw 200) and extending through the patient 30 to fluidly couple with the dosing reservoir 510. In some embodiments, the reservoir 510 is fluidly coupled to a drug delivery needle 515, and the reservoir 510 may be filled using a conventional syringe coupled to the needle 515. Some embodiments can include more than one reservoir 510 coupled to more than one tube 115. In some other embodiments, a reservoir 510 may be coupled to more than one dosing device 500. In some embodiments, the reservoir can include at least one drug. In some embodiments, more than one drug can be delivered to a patient from a single reservoir 510, whereas in other embodiments, one than one drug can be delivery to a patient using more than one reservoir, each reservoir 510 containing a different drug.

In some embodiments, any one of the cannulated screws or screw assemblies 200, 300, 400 described above and illustrated in FIGS. 2, 3A-3B, 4A-4B, 5A-5B, 6A-6B, 7A-7B, and 8A-8B can be used for therapy within any one of the cervical region of the human spine, the thoracic region of the human spine, the lumbar region of the human spine, and the sacral region of the human spine. Moreover, in some embodiments, any one of the cannulated screws or screw assemblies 200, 300, 400 described above and illustrated in FIGS. 2, 3A-3B, 4A-4B, 5A-5B, 6A-6B, 7A-7B, and 8A-8B can include inlet port 220a, 320a that may be used as an outlet to carry material from the screw or screw assemblies 200, 300, 400, and an outlet port 220b, 320b that may be used to carry material from the patient into the screw or screw assemblies 200, 300, 400.

For example, in some embodiments, any one of the cannulated screws or screw assemblies 200, 300, 400 described above and illustrated in FIGS. 2, 3A-3B, 4A-4B, 5A-5B, 6A-6B, 7A-7B, and 8 may be used in place of or in combination with a bone marrow aspirate kit such as the RETRIEVE® bone marrow aspirate kit for stem cell therapy.

In some embodiments of the invention, the cannulated screw 200, 300, 400 can comprise a biocompatible metal. In some embodiments, the biocompatible metal can be stainless steel, such as a surgical stainless steel. In other embodiments, other metals or metal alloys can be used based on at least one of iron, chromium, nickel, molybdenum, titanium, titanium alloys, or other group IV metals, and/or combinations thereof. In some other embodiments, the cannulated screw 200, 300 can comprise a polymer, a ceramic, a glass, a metal-matrix composite, or combinations thereof.

The invention claimed is:
1. A therapy delivery device comprising:
  a cannulated bone screw comprising a screw shaft including a screw thread, a proximal end, and a screw distal end including a tip;
  at least one channel extending through the screw shaft substantially parallel to a longitudinal axis of the screw shaft;
  at least one inlet port coupled to the at least one channel and extending through the proximal end;

at least one outlet port extending through the screw shaft and exiting at the screw distal end; and at least one valve coupled to the at least one channel and configured and arranged to control fluid flow out of the at least one channel wherein the valve comprises a plunger, the plunger comprising a plunger rod positioned within the screw shaft and a plunger first end and a plunger second end and a valve seat coupled to the plunger second end, wherein a wring is coupled to the plunger.

2. The therapy delivery device of claim 1, wherein the valve comprises a closed valve when the plunger is withdrawn wherein the valve seat is sealed against the screw distal end; and wherein the closed valve is configured and arranged to substantially prevent flow out of the channel.

3. The therapy delivery device of claim 1, wherein the valve comprises an open valve when the plunger is extended wherein the valve seat is positioned distal from the screw distal end; and wherein the open valve is configured and arranged to enable fluid flow out of the channel.

4. The therapy delivery device of claim 1, wherein a fluid flow rate through the valve and a fluid flow into and out of the cannulated screw is controlled by the plunger position within the screw shaft.

5. The therapy delivery device of claim 1, wherein the spring is configured and arranged to maintain the valve seat sealed against the distal end when the plunger is not forcibly extended.

6. The therapy delivery device of claim 1, wherein the spring is configured and arranged to expand when the plunger is forcibly extended.

7. The cannulated screw of claim 1, further comprising a temporary encasement at least partially covering the screw.

8. The cannulated screw of claim 7, wherein the temporary encasement envelops substantially all the screw thread.

9. The cannulated screw of claim 7, wherein the temporary encasement comprises wax.

10. The cannulated screw of claim 1, wherein the valve is bioresorbable.

11. The cannulated screw of claim 10, wherein the valve comprises polylactic acid.

12. The therapy delivery device of claim 1, wherein the plunger comprises bioresorbable material.

13. The therapy delivery device of claim 12, wherein the bioresorbable material includes a polylactic acid.

14. The therapy delivery device of claim 1, wherein travel of the plunger reduces pressure of a fluid contained within the therapy device.

15. A therapy delivery device comprising:

a cannulated bone screw comprising a screw shaft including a screw thread, a proximal end, and a screw distal end including a tip;

at least one channel extending through the screw shaft substantially parallel to the longitudinal axis of the screw shaft;

at least one inlet port coupled to the at least one channel and extending through the proximal end; at least one outlet port extending through the screw shaft and exiting at the screw distal end; and at least one valve coupled to the at least one channel and configured and arranged to control fluid flow out of the at least one channel wherein the valve comprises a plunger, the plunger comprising a plunger rod positioned within the screw shaft and a plunger first end and a plunger second end and a valve seat coupled to the plunger second end, and further comprising at least one subcutaneously implanted dosing reservoir and; at least one tube coupled to the channel and configured to extend through a patient to fluidly couple with the dosing reservoir.

16. The therapy delivery device of claim 15, wherein the reservoir is fluidly coupled to a drug delivery needle.

17. The therapy delivery device of claim 16, wherein the dosing reservoir includes a drug.

* * * * *